United States Patent [19]

Chagnon et al.

[11] Patent Number: 5,389,377
[45] Date of Patent: Feb. 14, 1995

[54] SOLID CARE THERAPEUTIC COMPOSITIONS AND METHODS FOR MAKING SAME

[75] Inventors: Mark S. Chagnon, Pelham, N.H.; John R. Ferris, Newburyport, Mass.; Tracy J. Hamilton; Edwin A. Rudd, both of Salem, N.H.; Michelle J. Carter, Derry, N.H.

[73] Assignee: Molecular Bioquest, Inc., Atkinson, N.H.

[21] Appl. No.: 958,646

[22] Filed: Oct. 7, 1992

Related U.S. Application Data

[63] Continuation-in-part of Ser. No. 894,260, Jun. 8, 1992, which is a continuation-in-part of Ser. No. 566,169, Aug. 10, 1990, abandoned, which is a continuation-in-part of Ser. No. 455,071, Dec. 22, 1989, abandoned.

[51] Int. Cl.$^6$ ............................................. A61K 9/127
[52] U.S. Cl. ................................... 424/450; 424/490; 424/498; 424/600; 424/617; 424/630; 424/635; 424/639; 424/641; 424/644; 424/646; 424/650; 428/402.24
[58] Field of Search ............... 424/450, 417, 420, 600, 424/641, 617; 428/402.2, 402.24, 490, 498, 630, 635, 639, 644, 646, 650

[56] References Cited

U.S. PATENT DOCUMENTS

| | | | |
|---|---|---|---|
| 4,331,654 | 5/1982 | Morris | 424/38 |
| 4,675,173 | 6/1987 | Widder . | |
| 4,839,111 | 6/1989 | Huang | 424/450 |
| 4,945,049 | 7/1990 | Hamaya et al. . | |
| 5,071,076 | 12/1991 | Chagnon et al. . | |
| 5,091,187 | 2/1992 | Haynes | 424/450 |

FOREIGN PATENT DOCUMENTS

| | | | |
|---|---|---|---|
| 0125995 | 11/1984 | European Pat. Off. | G01N 33/54 |
| 0546939 | 6/1993 | European Pat. Off. | A61K 49/00 |
| 8911335 | 11/1989 | WIPO | B01J 13/02 |
| 9109678 | 7/1991 | WIPO | B03C 1/00 |

OTHER PUBLICATIONS

Chan et al, "Magnetic Resonance Imaging of Abscesses Using Lipid-Coated Iron Oxide Parties", pp. 443–449, Jun. 1992.

Dinger et al, "Safety Profile of Gd-DTPA: Clinical Experience", Berlin, West Germany, Abstract only, Nov. 1990.

Tzika et al, "Ferrosomes: Long-lived Superparamagnetic MR Imaging Contrast Agent", San Francisco, Calif., Abstract, Nov. 1990.

Reimer et al, "Improved Detection of Liver Cancer with Hepatocyte-directed superparamagnetic Iron Oxide Particles" Charlestown, Mass., Abstract only, Nov. 1990.

Chan, et al, "MR Imaging of Abscess by Use of Lipid—coated Iron Oxide Particles", Philadelphia, Pa., Abstract only, Nov. 1990.

*Primary Examiner*—G. S. Kishore
*Attorney, Agent, or Firm*—Hayes, Soloway, Hennessey, Grossman & Hage

[57] ABSTRACT

A liposome composition which comprises a substantially uniform sized inorganic core coated with an amphipathic organic compound and further coated with a second amphipathic vesicle forming lipid. Also disclosed are novel phenyl lipid compounds which serve as the amphipathic vesicle forming lipid and methods are described for delivering a drug for slow release into the blood stream, and for targeting a selected tissue or cells with the inorganic core liposome compositions.

10 Claims, 2 Drawing Sheets

SOLID CARE THERAPEUTIC COMPOSITIONS AND METHODS FOR MAKING SAME

This application is a continuation-in-part of copending U.S. application Ser. No. 07/894,260, filed Jun. 8, 1992, which is a continuation-in-part of U.S. application Ser. No. 07/566,169, filed Aug. 10, 1990, now abandoned, which is a continuation-in-part of U.S. application Ser. No. 07/455,071, filed Dec. 22, 1989, now abandoned. Attention is also directed to commonly assigned, U.S. Pat. No. 5,225,282.

FIELD OF THE INVENTION

The present invention relates to the preparation of inorganic liposome therapeutic compositions, and, more particularly, to a method preparing uniform size inorganic liposomes for invivo and invitro medical applications.

BACKGROUND OF THE INVENTION

Lipids are molecules that consist of both hydrophobic and hydrophilic groups or regions within the same molecule. The ratio between the hydrophobic and hydrophilic portions of the molecule determines its physical properties in an aqueous environment. The uses of natural phospholipids as additives include, for example, food emulsifiers, cosmetics, industrial surfactants, and, and pharmaceutical drug-delivery systems. U.S. Pat. Nos. 4,086,257, 4,097,502, 4,097,503, 4,145,410 and 4,159,988 disclose various modifications of the polar-head-group region of natural phospholipids which lead to unique physical properties.

Various compounds prepared from lecithin have been described. For example, phosphatidyl polyethylene oxide compounds, their preparation and their use to encapsulate drugs in a drug-delivery system are mentioned in U.S. Pat. No. 4,426,330. Functionalized oxylalkylated lecithin and phosphatidyl-alkanolamine derivatives are described in U.S. Pat. Nos. 2,801,255, 3,542,820, 3,577,466 and 4,254,115.

Liposomes are microscopic spheres formed of thin durable lipid membranes. This membrane structure allows liposomes to regulate the passage of an entrapped drug into the bloodstream, a feature that offers potential for improving drug effectiveness and reducing side effects associated with certain drugs.

The emphasis of the bulk of liposome research is on injectable pharmaceutical products designed to improve the efficacy and reduce the toxicity of selected existing and new drugs used to treat cancer and infectious diseases. The use of liposomes and other lipid structures, such as micro-emulsions, micelles, and drug/lipid complexes, for drug delivery has been widely proposed. Such lipid structures, and particularly liposomes, have the potential for providing controlled release of an administered drug over an extended time period, and of reducing the side effects of the drug by limiting the concentration of free drug in the bloodstream. These advantages apply to a variety of routes of administration, including intravenous, intramuscular, and subcutaneous application to muscular tissue, or delivery by inhalation. Where liposomes are administered by intravenous delivery, liposomes provide a further advantage of altering the tissue distribution of the drug. Liposome drug delivery systems have been reviewed. See Gregoriadis, G., in Liposomes, vol III, Poznansky, M. L., et al, Pharm. Revs., 36(4):277 (1984).

In general, soon after entering the bloodstream, liposomes are recognized as foreign particles and removed from circulation by specialized cells residing primarily in the liver and spleen. These cells and organs are components of the reticuloendothelial system or "RES". Following uptake by the RES, the liposomes gradually release the drug in its free form back into the bloodstream. This RES uptake and release pattern is useful when the intent is to treat certain diseases which reside in the RES or to avoid a high concentration of the drug in the bloodstream. However, as a result of this RES-uptake mechanism, liposomes have not been shown to be as effective when it is desirable to target the drug to other parts of the body.

Several years ago it was recognized that liposomes capable of evading the RES-uptake mechanism might provide opportunities to develop new products with improved therapeutic profiles. Accordingly, research efforts were initiated to created methods for rendering liposomes delivered intravenously "invisible" to the RES, thereby increasing the circulation time of the liposome-entrapped drug in the bloodstream to improve the probability that drug-carrying liposomes will reach diseased tissues and organs.

One method for decreasing RES recognition of injected liposomes involves a specially synthesized polyethyleneglycol ("PEG") derivatized lipid, and the other involves a naturally occurring phosphatidylinositol ("PI") lipid. These PEG and PI molecules bind water molecules to the liposome surface. It is believed that this binding is the mechanism that disguises the liposomes from the RES and significantly increases blood circulation times as compared to both non-hydrophilized liposomes and the drug in its free form. See U.S. Pat. Nos. 4,426,330 and 4,534,899.

Hydrophilized liposomes may also provide significant improvements in the efficacy of certain cancer drugs, antibiotics and other therapeutics, while decreasing exposure of normal tissues to such drugs, thereby reducing some of the side effects associated with conventional therapies.

In the case of liposomes, optional size for use in parenteral administration is generally between about 100 nm and 300 nm. Liposomes in this size range can be sterilized by passage through conventional filters having a particle size discrimination of about 200 nm. This size range of liposomes also may favor biodistribution in certain target organs, such as liver, spleen and bone marrow, and gives more uniform and predictable drug-release rates and stability in the bloodstream. See, e.g., A. Gabizon, et al, J. Liposome Research 1:123 (1988). Liposomes whose sizes are less than about 300 nm also show less tendency to agglutinate on storage, and are thus generally safer and less toxic in parenteral use than larger size liposomes.

It may also be desirable to prepare uniform size liposomes in a selected size range less than about 100 nm. For example, small unilamellar vesicles (SUVs) having sizes between about 30–80 nm are useful in targeting to tumor tissue or to hepatocyte cells, because of their ability to penetrate the endothelial lining of capillaries. SUVs are also advantageous in opthamalic liposome formulations, because of the greater optical clarity of the smaller liposomes.

Sonication, or ultrasonic irradiation, is a known method that is used for reducing liposome sizes by shearing and especially for preparing SUVs. The processing capacity of this method is quite limited, however, since long-term sonication of relatively small volumes is required. Also, localized heat build-up during sonication can lead to peroxidative damage to the lipids, and sonic probes shed titanium particles which are potentially quite toxic in vivo.

A third general size-processing method known in the prior art is based on liposome extrusion through uniform pore-size polycarbonate membranes (F. Szoka, Jr., et al, Proc. Natl. Acad. Sci. USA 75:4194(1978)). This procedure has advantages over homogenization and sonication methods in that several membrane pore sizes are available for producing liposomes in different selected size ranges. In addition, the size distribution of the liposomes can be made quite narrow, particularly by cycling the material through the selected-size filter several times. Nonetheless, the membrane extrusion method has limitations in large-scale processing including problems of membrane clogging, membrane fragility, and relatively slow throughput.

U.S. Pat. No. 4,737,323 describes a liposome sizing method in which heterogeneous-size liposomes are sized by extrusion through an symmetric ceramic filter. This method allows greater throughput rates, and avoids problems of clogging since high extrusion pressure and reverse-direction flow can be employed. However, like the membrane extrusion method, the filter-extrusion method requires post-liposome formation sizing. Further, the method may be limited where uniform-size SUVs are desired.

One limitation of all of the above-mentioned methods in the loss of encapsulated material as large liposomes are broken and reformed as smaller vesicles. Furthermore, in none of the liposome-preparation methods mentioned above are liposomes with a narrow, substantially symmetrical size distribution produced, nor are liposomes produced with small enough uniform size to cross transcellular barriers. Finally, liposomes are known to be generally unstable and always exhibit uncontrolled leakage of drugs prior to reaching the delivery cite.

More recently, there have been investigations regarding the potential application of lipid-coated iron oxide particles as magnetic resonance contrast agents for imaging inflammatory processes. It has been shown, for example, that intravenous injections of lipid-coated iron oxide particles can serve as contrast agents and the effects on proton relaxation times have been reported. See, e.g. *MR Imaging of Absessess by Use of Lipid-coated Iron Oxide Particles*, Radiological Society of North America, 76th Annual Meeting, November (1990). In European Pat. No. 272,091 there is described an in vivo delivery vehicle which comprises as the delivery vehicle a superparamagnetic and ferromagnetic particle 20–10,000 nm in diameter, an amphiphilic material associated with said particles to form what is described as an amphiphilic-associated substrate, and an encapsulating layer including at least one such layer associated with the amphiphilic substrate, the outer of the encapsulating layers being a bio-compatible encapsulating layer. The specific targeting or delivery of the compound to particular tissues, organs or cells is reported, as well as extended circulation and serum stability.

It is therefore a general object of the invention to provide a novel uniform size inorganic core liposome composition of uniform size which solves or substantially overcomes problems associated with the prior art. It is a more specific object of this invention to provide a liposome with an inorganic core of substantially uniform sub 100 nm size, shape, charge and chemistry which can be used for invivo and invitro medical applications (e.g., the administering of a drug via the bloodstream), and a process for making them. Another object of the invention is to provide a method of preparing a uniform size inorganic liposome composition without requiring post-liposome formation extrusion or other sizing procedures. Still another object of the invention is to provide such a method which can be practiced to achieve relatively high encapsulation rates, and in which loss of non-encapsulated material is avoided.

It is also an object of the invention to provide a novel phenyl lipid composition with enhanced circulation time in the bloodstream, and to the method of preparation and to the use of such compounds, particularly in solubilizing, in an aqueous environment, water-insoluble compounds, and to the use of such phenyl lipid compounds for modifying the solubility of the uniform size inorganic core liposome composition.

SUMMARY OF THE INVENTION

It has now been found that the inorganic oxides of substantially uniform particle size reported in co-pending application Ser. No. 07/894,260 can be used to prepare a liposome composition comprising a substantially uniform size inorganic core coated with an amphipathic organic compound and further coated with a second amphipathic vesicle forming lipid. The inorganic core is again prepared by contacting aqueous solutions of an inorganic salt and an inorganic base across a porous membrane wherein the membrane contains a plurality of pores which allows for precipitation of substantially monodispersed size inorganic oxide particles on one side of the membrane and precipitation of a salt of the corresponding base on a second side of the membrane. Inorganic cores are also prepared by the reaction of metallocenes with aqueous metal hydroxide slurries followed by milling to uniform particle size. The class of inorganic cores include $Fe_3O_4$, $Fe_2O_3$, $Al_2O_3$, $TiO_2$, $ZnO$, $FeO$, and $Fe$.

The amphipathic vesicle forming lipid is preferably a lipid having two hydrocarbon chains, including acyl chains, and a polar head group. Included in this class are the phospholipids, such a phosphatidylcholine (PC), phosphatidic acid (PA), phosphatidylinositol (PI), sphingomyelin (SM), and the glycolipids, such as cerebroside and gangliosides.

The amphipathic vesicle forming lipid can also be novel synthetic phenyl lipid compound having the structural formula:

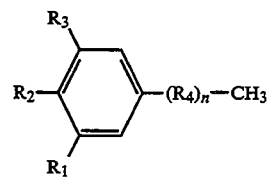

wherein two of $R_1$, $R_2$ and $R_3$ represent a saturated or unsaturated straight-chain or branched chain alkyl or acyl group, the other being hydrogen, therein providing at least two hydrocarbon chains attached to the phenyl moiety, wherein the two hydrocarbon chains are typically between about 14–22 carbon atoms in length, and have varying degrees of unsaturation. $R_4$ represents the repeating unit of either a poly(alkylene oxide) polymer, preferably ethylene, propylene and mixtures thereof, or the repeating unit of poly(vinyl alcohol). The number of alkylene oxide or vinyl alcohol groups in the polymer, designated as n, may vary from 0 to about 200 or more.

In a further aspect, the invention includes an inorganic core liposome composition for administering drugs via the bloodstream, comprising a substantially uniform size inorganic core coated with an amphipathic organic compound and further coated with 1-20 mole percent of an amphipathic vesicle-forming lipid derivatized with a hydrophilic polymer, and containing the compound in liposome-entrapped form.

These and other objects and features of the invention will become more fully apparent when the following detailed description of the invention is read in conjunction with the accompanying drawings.

DETAILED DESCRIPTION OF THE INVENTION

I. Definitions

Figure 1:
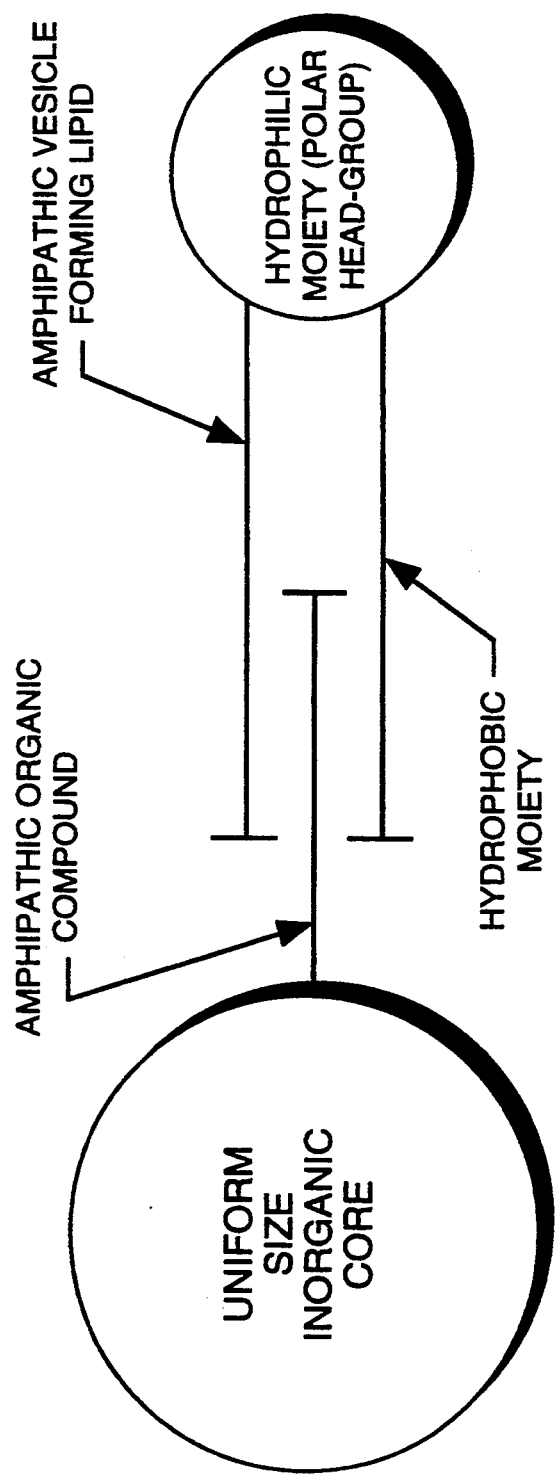
FIG. 1 illustrates the general liposome composition comprising a substantially uniform size inorganic core coated with an amphipathic organic compound and further coated with an amphipathic vesicle forming lipid.

As used herein the term:

"Polyalkylether" refers to polyethyleneglycol and related homopolymers, such as polymethylethyleneglycol, polyhydroxypropyleneglycol, polypropyleneglycol, polymethylpropyleneglycol, and polyhydroxypropyleneoxide, and to heteropolymers of small alkoxy monomers, such as polyethylene/polypropyleneglycol, such polymers having a molecular weight of at least about 120 daltons, and up to about 20,000 daltons.

"Amphipathic organic compound" refers to any organic compound containing both a hydrophobic and hydrophilic moiety.

"Amphipathic vesicle forming lipid" refers to any lipid having a hydrophobic unit and hydrophilic unit, the hydrophobic group typically including two acyl hydrocarbon chains, the hydrophilic group containing a reactive chemical group such as amine, acid, ester, aldehyde, or alcohol group by which the lipid can be derivatized, e.g. to a polyalkylether.

II. Preparation of Uniform Size Inorganic Core

Uniform size inorganic core particles can be prepared by the preferred method reported in co-pending, and commonly assigned parent application 07/894,260, filed Jun. 8, 1992, the teachings of which are incorporated by reference. As described therein, aqueous solutions of an inorganic salt and an inorganic base are contacted across a porous membrane wherein the membrane contains a plurality of pores which allows for precipitation of substantially monodispersed inorganic oxide particles on one side of the membrane and precipitation of a salt of the corresponding base on a second side of the membrane. Particle size diameter can range between 5–1000 Angstroms, and in a preferred embodiment, 5–100 Angstroms, with a particle size distribution of ±10%. The inorganic salts are of the formula MY, wherein M is selected from the group consisting of Fe, Co, Ni, Zn, Mn, Mg, Ca, Ba, Sr, Cd, Hg, Al, B, Sc, Ga, V, In, and mixtures thereof, with Y being selected from the group consisting of Cl, Br, I, $SO_4$, $NO_3$, $PO_4$ and mixtures thereof. The inorganic base is selected from the group consisting of $NH_4OH$, KOH, LiOH, NaOH, CsOH, RbOH and mixtures thereof. Accordingly, and in a preferred embodiment, $Fe_3O_4$ is prepared (a mixed Fe(+2)Fe(+3) oxide of the formula [Fe(+2)][Fe(+3)]$_2O_4$) with a uniform sub 100 Angstroms diameter serving as the inorganic core of the liposomes described herein.

Inorganic core particles can also be prepared according to the following general procedure: metal salts, or organometallocenes are precipitated in base at high temperature and pressure to form fine magnetic metal oxide crystals. The crystals are redispersed, then washed in water and an electrolyte. Magnetic separation can be used to collect the crystal between washes. The crystals are then milled to a more controlled particle size, for example, in a ball mill, under conditions sufficient to form 50 Angstroms or lower particle size. See, commonly assigned U.S. Pat. No. 5,071,076, and copending application Ser. No. 07/806,478, filed Dec. 13, 1991, now U.S. Pat. No. 5,225,282 the teachings of which are incorporated by reference.

III. Amphipathic Organic Compounds

The amphipathic organic compounds which can be used in forming the inorganic core liposome of the invention may be selected from a variety of organic compounds which contain both a hydrophobic and hydrophilic moiety. According to one important aspect of the invention, it has been discovered that the hydrophilic moiety is adsorbed or coordinated onto the surface of the inorganic oxide, whereas the hydrophobic moiety of the molecule extends outwardly to associate with the amphipathic vesicle forming lipid compounds. Preferred amphipathic organic compounds include fatty acids selected from the group consisting of oleic, stearic, linoleic, lionlenic, palmitic, nyristic and arachidonic acid.

IV. Amphipathic Vesicle Forming Lipid Components

The lipid components used in forming the inorganic core liposomes of the invention may be selected from a variety of vesicle forming lipids, typically including phospholipids, such as phosphatidylcholine (PC), phosphatidic (PA), phosphatidylinositol (PI), sphinogomyelin (SM), and the glycolipids, such as cerebroside and gangliosides. The selection of lipids is guided by consideration of (a) drug release rate is serum, (b) drug-entrapment efficiency, (c) liposome toxicity, and (d) biodistribution and targeting properties. A variety of lipids having selected chain compositions are commercially available or may be obtained by standard lipid isolation procedures. See, e.g. U.S. Pat. No. 4,994,213.

The lipids may be either fluidic lipids, e.g. phospholipids whose acyl chains are relatively unsaturated, or more rigidifying membrane lipids, such as highly saturated phospholipids. Accordingly, the vesicle forming lipids may also be selected to achieve a selected degree of fluidity or rigidity to control the stability of the liposome in serum and the rate of release of entrapped drug from the liposome in the bloodstream. See, e.g. U.S. Pat. No. 5,013,556.

In a preferred embodiment, the vesicle forming lipid include those phospholipids in which the polar-headgroup region is modified by the covalent attachment of polyalkylene ether polymers of various molecular weights. The attachment of the relatively hydrophilic polyalkylene ether polymer, particularly polyethylene oxide, alters the hydrophilic to hydrophobic balance within the phospholipid in order to give unique solubility to the phospholipid compound in an aqueous environment. See, e.g. U.S. Pat. No. 4,426,330. The polyalkyl ether lipid is preferably employed in the inorganic core liposome composition in an amount between about 1–20 mole percent, on the basis of moles of derivatized lipid as a percentage of total moles of vesicle-forming lipids. The polyalkylether moiety of the lipid preferably has a molecular weight between about 120–20,000 daltons, and more preferably between about 1000–5000 daltons.

In yet another embodiment of the present invention, a new series of phenyl lipid compounds are described which have the following structural formula:

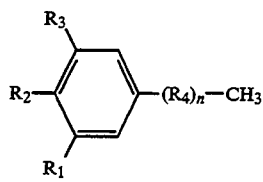

wherein two of $R_1$, $R_2$ and $R_3$ represent a saturated or unsaturated straight-chain or branched chain hydrocarbon group, the other being hydrogen, therein providing at least two hydrocarbon chains attached to the phenyl moiety, wherein the two hydrocarbon chains are typically between about 14–22 carbon atoms in length, and have varying degrees of unsaturation. $R_4$ represents the repeating unit of either a poly(alkylene oxide) polymer, preferably ethylene, propylene and mixtures thereof, or the repeating unit of poly(vinyl alcohol). The number of alkylene oxide or vinyl alcohol groups in the polymer, designated as n, may vary from 0 to about 200 or more.

V. Preparing the Inorganic Core Liposome Composition

One preferred method for producing the uniform size inorganic core liposome composition begins with first coating the magnetic particles described above in Section II with an amphipathic organic compound which contains both a hydrophillic and hydrophobic moiety. For example, fatty acids, such as oleic acid, linoleic acid or linolenic acid, dispersed in an organic solvent, are directly added to the particles at a ratio of dry $Fe_3O_4$:acid equal to 2:1 weight percent. After mechanically milling the mixture for 1 to 1.5 hours on a ball mill with 4 mm glass media, the acid coated particles collapse around the media allowing for easy removal of water without the loss of the particles. The coated particles are then dispersed in an organic solvent by addition of 700 ml of hexane, toluene or chloroform and mechanically milling with glass media overnight (15 hrs).

Absorbing a phospholipid onto the fatty acid coated particles was accomplished by addition of a synthetic polyethylene glycol terminated phosphatidyl ethanolamine to the above dispersion and mechanically mixing for 3 hours. The ratio of fatty acid:pure lipid is about 1:1 weight percent.

To transfer the particles from an organic phase to an aqueous phase, 7 mls of the dispersion was placed into a 14 ml glass vial with 3 ml of distilled water. The vial was placed in warm, 35° C. sonicating water bath with $N_2$ bubbling through it to evaporate the solvent. Once the solvent has evaporated, the aqueous dispersion was then suspended in a total of 10 mls of autoclaved water, sonicated for one hour, and centrifuged for 5 minutes. The supernatant was removed and brought to 20 mg particle/ml solution with autoclaved water.

IV. Utility

From the above, it can be appreciated that the present invention offers a number of advantages over prior art liposome-methods. The preparation of uniform size inorganic core particles by dialysis and precipitation across a semi-permeable membrane is unique in its ability to allow for the production of uniform size liposomes without the requirement for extrusion or other additional liposome sizing techniques. The ability to selectively vary the average size of liposomes, according to lipid composition and/or ionic strength, is another useful feature of the invention. While the present invention provides inorganic core liposomes with a size range of about 5–5000 nm, one selected size range, between about 100–300 nm, is particularly useful for a variety of parenteral uses, as discussed.

One general class of drugs include water-soluble liposome permeable compounds which are characterized by a tendency to partition preferentially into the aqueous compartments of the liposome suspension, and to equilibrate, over time, between the inner liposomal spaces and outer bulk phase of the suspension. Representative drugs in this class include terbutaline, albuterol, stropine methyl nitrate, cromolyn sodium, propracalol, funoisolide, ibuprofin, geniamycin, tobermycin, pentamidine, penicillin, theophylline, bleomycin, etopoxide, captoprel, n-acetyl cystein, verapamil, vitamins, and radio-opaque and particle-emitter agents, such as chelated metals. Because of the tendency of these agents to equilibrate with the aqueous composition of the medium, it is preferred to store the liposome composition in lyophilized form, with rehydration shortly before administration.

A second general class of drugs are those which are water-soluble, but liposome-impermeable. For the most part, these are peptide or protein molecules, such as peptide hormones, enzymes, enzyme inhibitors, apolipoproteins, and higher molecular weight carbohydrates characterized by long-term stability of encapsulation. Representative compounds in this class include calcitonin, atriopeptin, $\alpha$-1 antitrypsin (protease inhibitor), interferon, oxytocin, vasopressin, insulin, interleukin-2, superoxide dismutase, tissue plasminogen activator (TPA), plasma factor 8, epidermal growth factor, tumor necrosis factor, lung surfactant protein, interferon, lipocortin, $\alpha$-interferon, macrophage colony stimulating factor, and erythroprotein.

A third class of drugs are lipophilic molecules. The drugs in this class are defined by an oil/water partition coefficient, as measured in a standard oil/water mixture such as octanol/water, of greater than 1 and preferably greater than about 5. Representative drugs include prostaglandins, amphotericin B, progesterone, isosorbide dinitrate, testosterone, nitroglycerin, estradiol, doxorubicin, epirubicin, beclomethasone and esters, vitamin E, cortisone, dexamethasone and esters, and betamethasone valerete.

In another application, the inorganic core liposome composition is designed for targeting a specific target tissue or organ. For example, this feature allows for targeting a tumor tissue, for drug treatment by intravenous administration to a tumor-bearing subject.

As another example, the inorganic core liposomes may be prepared with surface-bound ligand molecules, such as antibodies, which are effective to bind specifically and with high affinity to ligand-binding molecules such as antigens, which are localized specifically on target cells.

A variety of methods for coupling ligands to the surface of liposomes are known, including the incorporation of ligand-derivatized lipid components into liposomes or coupling of ligands to activated liposome surface components.

The targeted inorganic core liposomes may be prepared to include cancer chemotherapeutic agents, such as those listed above. In one preferred embodiment, the liposomes are prepared to include PEG-PE and PG, to a final concentration of charged lipids up to 40 mole percent, doxorubicin, and remainder neutral phospholipids or neutral phospholipids and cholesterol.

In an inorganic core liposome composition which is useful for radio-imaging of solid tumor regions, the liposomes are prepared with encapsulated radio-opaque or particle-emission metal, typically in a chelated form which substantially prevents a permeation through the liposome bilayer.

In still another application, the liposome composition is designed to enhance uptake of circulating cells or other blood-borne particles, such as bacteria, virus-infected blood cells and the like. Here the long-life liposomes are prepared to include surface-bound ligand molecules, as above, which bind specifically and with high affinity to the selected blood-borne cells. Once bound to the blood-borne particles, the liposomes can enhance uptake by the RES.

Polyalkylether moieties on the liposomes may be derivatized by the associated amphipathic lipid by an ester, peptide, or disulfide bond which can be cleaved, after liposome binding, to the target cells, to further enhance RES particle clearance.

Studies performed in support of the present invention indicate that the inorganic core liposome composition of the invention provides an enhancement in blood circulation lifetime which is equal, and in some cases superior, to the most effective RES-evading rigid-lipid liposomes which have been reported heretofore, including liposomes containing GMI and membrane-rigidifying lipids.

The blood circulation lifetimes achieved in the present invention should be substantially greater than with fluid-core liposomes.

The following examples illustrate methods of preparation of inorganic core liposomes with enhanced circulation times, and for accessing circulation times in vivo and invitro. The examples are intended to illustrate specific inorganic-core liposome compositions and methods of the invention, but are in no way intended to limit the scope thereof.

DESCRIPTION OF THE EMBODIMENTS

Example 1

Preparation of Magnetic Particles by Co-precipitation of Fe+2/Fe+3 with Excess Base Magnetic particles of 100 Angstroms in diameter are prepared using the following method. Iron salts, $FeCl_2$—, $3H_2O$, (25 g), and $FeCl_3$ (41 g) are each dissolved in 1000 cc of water. The solutions are combined into a 2 liter beaker and 70 ml of ammonium hydroxide is added while mixing. The resulting black magnetic precipitate yields 28 gm of magnetite, $Fe_3O_4$.

Example 2

Preparation of sub 10 nm particles 2 nm diameter uniform magnetic crystals were prepared by controlled contact of a base solution and iron salt solution across a semipermeable membrane, resulting in an iron oxide crystal precipitate of defined size within a narrow size distribution range.

A Spectra/Por 5 dialysis membrane (flat sheet) was affixed in a manner as to separate two equal sized chambers of a two sided Dialysis reaction tank. Both sides of the tank were filled with 20 liters of distilled $H_2O$ at 20° C. 12.5 g $FeCl_2$—$4H_2O$ and 20 g $FeCl_3$ were added to one chamber of the tank and stirred until dissolved. 60.6 g NaOH were dissolved in 2 liters of $H_2O$ and added to the solution into the opposite chamber in the tank. Both sides were agitated by a mechanical paddle stirrer for 15 min. After 70–80 hours of contact time, the iron solution and precipitated crystals were removed from the tank and the magnetic crystals were collected by centrifugation and measures by TEM to be 2 nm average diameter.

Example 3

Preparation of Oleic Acid Coated Magnetite

Magnetic particles, $Fe_3O_4$, coated with oleic acid are prepared using magnetite as precipitated in Example 1. The magnetite is water washed by successive additions of distilled water to a slurry concentrate of magnetite. The beaker containing the magnetite slurry is place onto a permanent magnet to magnetically separate the magnetic particle from the salt by-products between each successive addition of water. After resting the slurry on the magnet for 5 minutes, the aqueous salt solution is decanted. The precipitate is then resuspended with agitation in a total of 1500 cc of water and placed on a permanent magnet for 5 minutes before decanting. The above washing process is repeated three additional times with water. After the final water wash is decanted, the particles are acetone washed and hexane washed a total of 5 times each in the above manner.

Oleic acid is added to the magnetic hexane slurry in a ratio of oleic acid:dry particle equal to 2:1 weight percent. The mixture is adjusted to 15% total solids with hexane and mechanically milled overnight in a glass jar half filled with 3 mm stainless steel media.

Example 4

Preparation of Oleic Acid Coated Dialyzed Magnetic Particles

Dialyzed particles coated with oleic acid are prepared using particles as prepared in Example 2. 0.1 grams of particles are washed with three 200 ml volumes of distilled water and acetone by suspending approximately 0.1 gm dry particle in 200 ml of acetone and centrifuging for 45 minutes to collect particles between each washing.

Oleic acid was added to the acetone slurry in a ratio of oleic acid:dry particle equal to 2:1 weight percent and mechanically milled overnight in a glass jar half filled with 3 mm glass media.

Example 5

Preparation of Magnetite Core Liposomes using Phosphatidyl Choline 10 gms Oleic acid coated magnetite as prepared in Example 3 was dispersed in 100 cc hexane. The phosphate lipid is absorbed onto the particle by dissolving phosphatidyl choline (Sigma, P-3644, L-2, lechithin, 45% PC) into hexane with heating to create a 15% solution. The PC/hexane solution is combined with the magnetic/hexane solution at a ratio of pure phosphatidyl choline:oleic acid equal to 1:2 weight percent.

The solution was mixed in a glass jar (without media) on a jar roller for two hours. After mixing, the lipid was absorbed onto the particle by adding three times as much acetone as hexane and collecting the lipid coated particles over a magnet. After the coated magnetic particles were separated from the solvents, the solvents were decanted, distilled water was added to produce a 2.0% TS slurry. The slurry is heated in a beaker on a hot plate to 100° C. for 10 min. From 0.5 to 50 grams of triton x-114 (Union Carbide) was added to disperse the lipidized magnetic particles in an aqueous system. A ratio of triton x114:lipid particle equal to 1:6 weight percent was the optimum level for the dispersion. The dispersion was mixed on a laboratory vortex mixer for 2 minutes and placed in an ultrasonic bath (Branson 1200, VWR) for two hours. The final dispersion is adjusted to 0.2% TS (2 mg/ml). Particles were measured on a Nycomp laser particle size analyzer and were found to be approximately 200 nm in diameter.

Example 6

Preparation of Phenyl Lipid

A. Synthesis of a m-isophthalic acid based phenyl lipid

The starting material for this synthesis if 5-Aminoisophthalic acid. The 5-aminoisophthalic acid is not soluble in dioxane alone. It is soluble in a mixture of dioxane and triethylene glycol. 5-aminoisophthalic acid (145 mg) was dissolved in 5 ml. of dioxane and 2 ml. of triethylene glycol, and the pH was adjusted to 10 with NaOH. Methoxypolyoxyethylene imidazoly carbonyl, average mol. wt. 5,000 from Sigma (2.0 g) was dissolved in 2 ml of H$_2$O, 1.0 ml of 1N Na$_2$CO$_3$, and 2.0 ml of triethylene glycol. This solution was added to the 5-aminoisophthalic acid solution and stirred for 36 hours at room temperature. The reaction mixture was then dialyzed overnight against 2 liters of H$_2$O. The dialyzed reaction mixture was mixed with 100 ml of pyridine and the liquids removed via rotary evaporation. The resulting yellow oil was placed in the refrigerator. After several days a white precipitate formed. The precipitate contains both coupled and uncoupled PEG.

Figure 2:
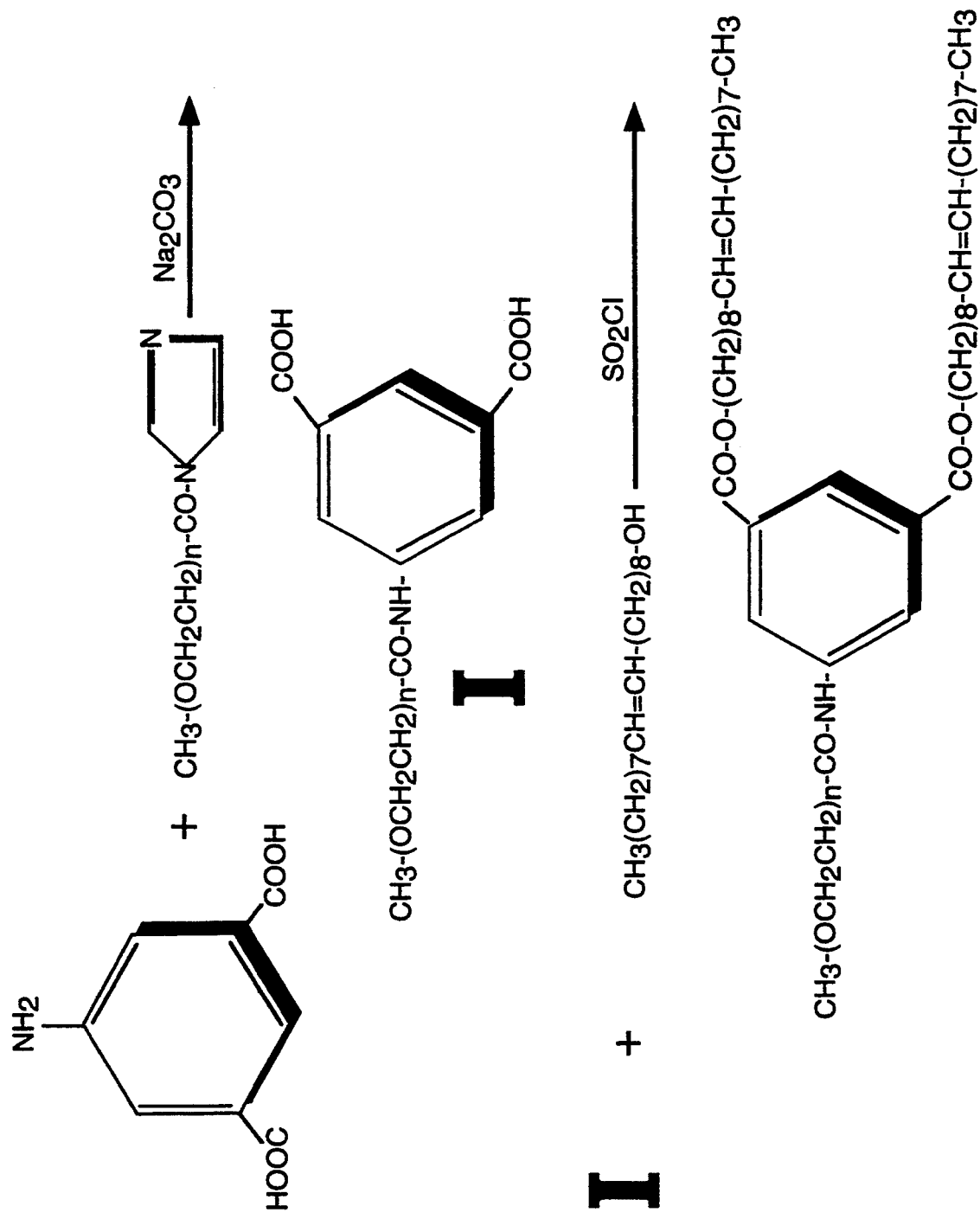
FIG. 2 is a reaction scheme for preparing a phenyl lipid derivatized with polyethyleneglycol.

Oleyl alcohol can be coupled to the above isophthalic acid derivative using thionyl chloride. The thionyl chloride can be used to activate the oleyl alcohol for ester formation with the carboxyl groups of the isophthalate. See. FIG. 2.

B. Synthesis of ortho phenyl lipids

The ortho analog of the phenyl lips can be synthesized starting with either 3,4 dihydroxybenzaldehyde or 3,4 dihydroxybenzoic acid. The aldehyde group can be coupled to an amino group by forming the Schiff's base and then reducing it with NaBH$_4$. Olegic acid could then be coupled to the hydroxyl groups using thionyl chloride to provide:

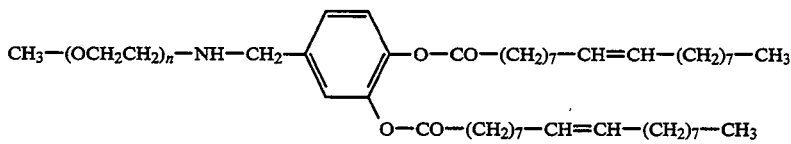

3,4 dihydroxybenzolic acid could be coupled through its carboxyl group to amino-terminated PEG using dicyclohexyl carbodiimide. Oleic acid could then be coupled as above.

Since both amino and carboxyl PEG derivatives as well as both oleic acid and oleylamine are available, the PEG and oleic acid groups can be easily interchanged in the above compounds.

Although the invention has been described and illustrated with respect to particular derivatized lipid compounds, liposome composition and use, it will be appreciated that a variety of modifications and changes may be made without departing from the invention.

We claim:

1. A solid core therapeutic composition for in vivo and in vitro applications comprising a substantially uniform size inorganic core selected from the group consisting of metals and metal oxides of Fe, Co, Ni, Zn, Mn, Mg, Ca, Ba, Sr, Cd, Hg, Al, B, Sc, Ga, V, and In, and mixtures thereof, characterized in that said core is capable of adsorbing or coordinating with a hydrophilic moiety, coated with a first amphipathic organic compound, characterized in that said first amphipathic organic compound contains a hydrophilic moiety and a hydrophobic moiety and the hydrophilic moiety is adsorbed or coordinated with the inorganic core and the hydrophobic moiety thereby extends outwardly from the inorganic core, and further coated with a second amphipathic compound wherein said second amphipathic compound contains a hydrophobic and hydrophilic moiety and the hydrophobic moiety associates with the outwardly extending hydrophobic moiety of said first amphipathic compound to form said solid core therapeutic composition.

2. The composition of claim 1 wherein the inorganic core is selected from the group consisting of Fe$_3$O$_4$, Fe$_2$O$_3$, Al$_2$O$_3$, TiO$_2$, ZnO, FeO and Fe.

3. The composition of claim 1 wherein the inorganic core is an inorganic oxide with a diameter of less than 100 nm.

4. The composition of claim 1 wherein the amphipathic organic compound is a fatty acid selected from the group consisting of oleic, linoleic, linolenic, palmitic, myristic and arachidonic acid.

5. The composition of claim 1 wherein the second amphipathic compound is selected from the group consisting of phospholipids, glycolipids, and mixtures thereof.

6. The composition of claim 5 wherein the phospholipid is selected from the group consisting of phosphatidylcholine, phosphatidic acid and phosphatidylinositol.

7. A solid core therapeutic composition for in vivo and in vitro medical applications comprising a substantially uniform size inorganic core selected from the group consisting of metals and metal oxides of Fe, Co, Ni, Zn, Mn, Mg, Ca, Ba, Sr, Cd, Hg, Al, B, Sc, Ga, V, and In, and mixtures thereof, a first amphipathic organic compound selected from the group consisting of fatty acid compounds, and further coated with a second amphipathic compound selected from the group consisting of phospholipids, glycolipids, and mixtures thereof, characterized in that said solid core therapeutic composition has a size range of about 5-5000 nm.

8. The solid core therapeutic composition of claim 7 wherein the fatty acid compound is selected from the group consisting of oleic, linolenic, palmitic, myristic and arachidonic acid and mixtures thereof.

9. The solid core therapeutic composition of claim 7 wherein the pholpholid is selected from the group consisting of phosphatidylcholine, phosphatidic acid and phosphatidylinositol and mixtures thereof.

10. The solid core therapeutic composition of claim 7 wherein the substantially uniform size inorganic core has a diameter of less than 100 nm.

* * * * *

UNITED STATES PATENT AND TRADEMARK OFFICE
CERTIFICATE OF CORRECTION

PATENT NO. : 5,389,377
DATED : February 14, 1995
INVENTOR(S) : Chagnon et al

It is certified that error appears in the above-indentified patent and that said Letters Patent is hereby corrected as shown below:

On the title page: Item [54]
line 1, "CARE" should be --CORE--

Col. 1, line 2, "CARE" should be --CORE--

Claim 5, Col. 12, line 63, after "phospholipids," insert --cholesterol, and--

Signed and Sealed this

Sixteenth Day of January, 1996

Attest:

BRUCE LEHMAN

*Attesting Officer*   *Commissioner of Patents and Trademarks*